United States Patent [19]

Dang Vu et al.

[11] Patent Number: 4,544,544

[45] Date of Patent: Oct. 1, 1985

[54] PLATE REACTORS FOR CHEMICAL SYNTHESES UNDER HIGH PRESSURE IN GASEOUS PHASE AND WITH HETEROGENEOUS CATALYSIS

[75] Inventors: Quang Dang Vu, Neuilly sur Seine; Claude Pradel, Rueil-Malmaison; Jean-Paul Euzen, Dardilly; Jean-François Le Page, Rueil-Malmaison, all of France

[73] Assignee: Institut Francais du Petrole, Rueil-Malmaison, France

[21] Appl. No.: 555,260

[22] Filed: Nov. 25, 1983

[30] Foreign Application Priority Data

Nov. 26, 1982 [FR] France .................................. 82 20026

[51] Int. Cl.$^4$ ............................ C01B 3/12; C01C 1/04
[52] U.S. Cl. ..................................... 423/659; 423/360
[58] Field of Search ........................ 423/659, 360, 361; 422/148, 200, 212

[56] References Cited

U.S. PATENT DOCUMENTS

| | | | |
|---|---|---|---|
| 2,887,365 | 5/1959 | De Rycker et al. | 422/148 |
| 3,472,631 | 10/1969 | Schober | 422/148 |
| 3,556,738 | 1/1971 | Schober | 422/148 |
| 3,932,139 | 1/1976 | Vilceanu et al. | 423/361 X |
| 4,180,543 | 12/1979 | Ward | 423/361 X |
| 4,452,760 | 6/1984 | Peterson et al. | 422/148 |

*Primary Examiner*—Donald R. Valentine
*Attorney, Agent, or Firm*—Millen & White

[57] ABSTRACT

The invention relates to a process and to an apparatus for effecting chemical syntheses in gaseous phase, under pressure, in the presence of a solid catalyst, for instance, for ammonia synthesis from hydrogen and nitrogen or for the synthesis of methanol or higher homolog alcohols from hydrogen and at least one carbon oxide.

The reactor (8) of substantially cylindrical shape, (see FIG. 4) contains a plurality of elongate compartments (9) of parallelipiped shape, adjacent to each other, the adjacent walls of the compartments or the common walls of the adjacent compartments being gas-tight walls (1), said tight walls forming hollow plates wherein are provided channels for the flow of a fluid heat carrier flowing through said walls under a pressure substantially equal to the pressure to which are subjected the reaction gases.

16 Claims, 7 Drawing Figures

PLATE REACTORS FOR CHEMICAL SYNTHESES UNDER HIGH PRESSURE IN GASEOUS PHASE AND WITH HETEROGENEOUS CATALYSIS

BACKGROUND OF THE INVENTION

This invention relates to a process and the corresponding apparatus for effecting chemical syntheses under high pressure with heterogeneous catalysis, from such gases as, for example, mixtures of hydrogen and carbon oxides or mixtures of hydrogen and nitrogen. The reaction zone is equipped with heat exchange plates and is essentially characterized in that:

The plates are connected to one another and to an external heat exchange apparatus, the assembly forming an exchange loop wherethrough flows a fluid heat carrier.

The fluid heat carrier inside the loop is subjected to a pressure substantially equal to that of the reaction gases, for example, the synthesis gases, preferably by establishing communication between the expansion chamber of the fluid heat carrier and, for example, the gas inlet into the reactor.

The plates which are plane are arranged either parallel to one another, or so to form enclosures of parallelipiped shape.

Some of these plates may be tightly connected to the inner wall of the reactor, the assembly thus forming a deflected path wherethrough the gas is compelled to flow.

In view of their better compacity and mainly in view of the extensive mechanization which can be used during their manufacture, these plate apparatuses, during the last years, have been preferred to the tube-and-shell apparatuses in many fields of thermal exchange.

In the field of the reactors, the use of plate apparatuses remains however rare and uncommon.

Thus, there has been proposed (French Pat. No. 1 438 723) a type of reactor made of a piling of layers, some of which may contain the catalyst whereas the others determine channels for the flow of the heat-conveying agent. The different layers are separated by subtantially plane plates.

This type of reactor, although of easy manufacture and of moderate price, remains however of limited use in view of its resistance to internal pressure.

SUMMARY OF THE INVENTION

The process of the invention have the purpose of extending the application of the plate apparatuses to the field of the high pressure synthesis reactions.

As a matter of fact, nearly all the main chemical basic products such as, for example, methanol and ammonia are manufactured under very high pressure.

In addition, under very high pressure the space is costly and the compacity of the plate exchangers constitutes a critical advantage.

BRIEF DESCRIPTION OF THE DRAWINGS

Reference will be made to the diagrammatical view of the figures.

Figure 1:
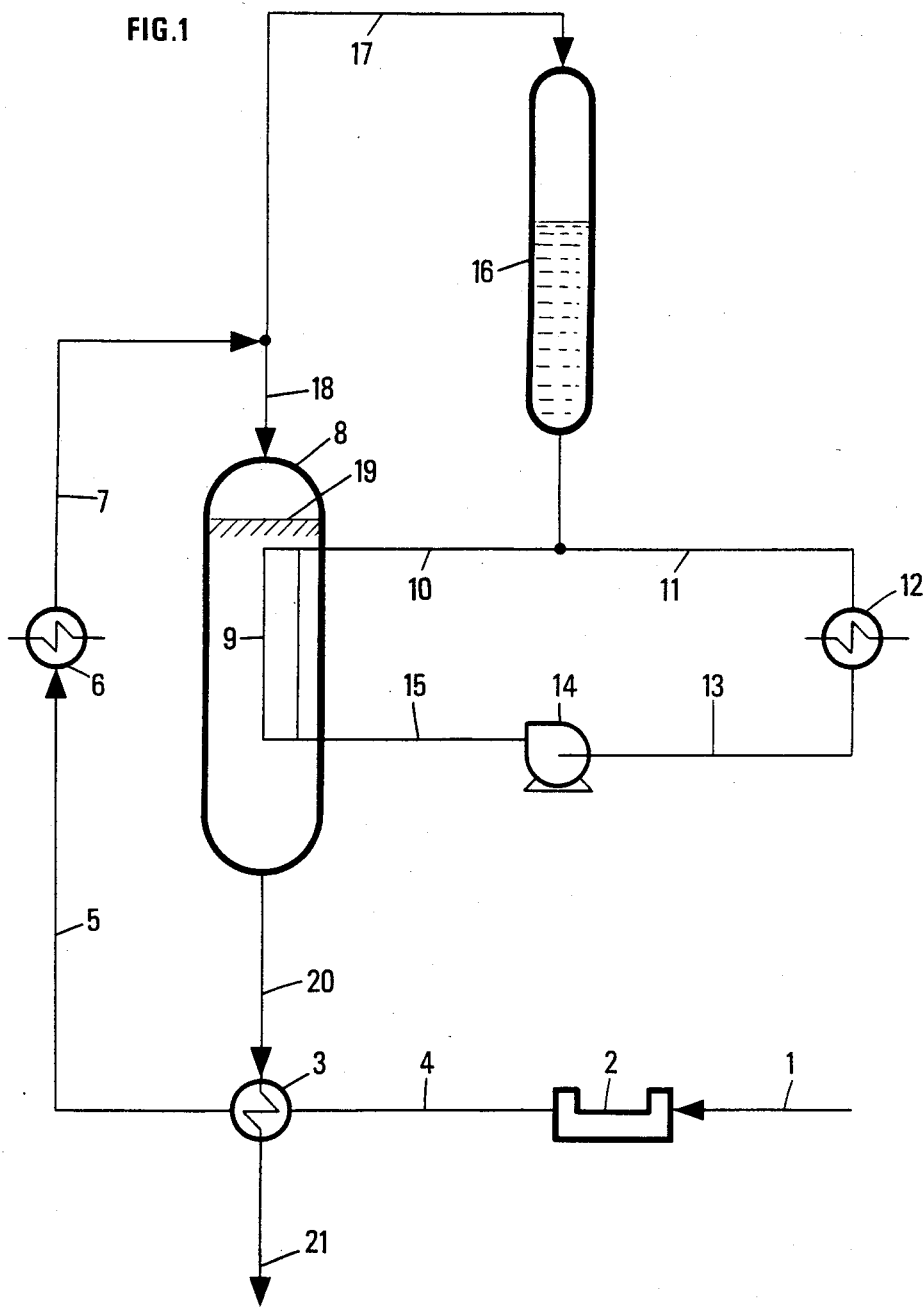
FIG. 1 illustrates conducting the process according to the present invention.

The mixture 1 of the synthesis gases, for example either hydrogen and at least one carbon oxide or hydrogen and nitrogen, is first conveniently brought to the desired pressure by means of compressor 2 and to the desired temperature by means of the exchangers between charge and effluent 3 and the reheater 6, by circulation through lines 4 and 5.

It is then introduced, through lines 7 and 18, into reactor 8, defining a cylindrical space and containing a bed 19 of solid catalyst. By contact with the catalyst, the gases react and the synthesis is effected. The reaction product is withdrawn through lines 20 and 21. The description of the reaction zone, according to the invention, is given hereinafter.

As the reaction proceeds, the temperature of the gases tends to vary as a result of the reaction heat, either evolved or absorbed. The gases are maintained under good operating conditions by thermal exchange with the heat exchange plates such as 9. These plates 9, arranged parallelly to the axis of the reactor cylinder, are connected on the one hand to one another and on the other hand to an apparatus (shown diagrammatically as 12) for heat exchange with the outside.

Fluid heat carrier destined to transfer heat from reactor 8 to exchanger 12 is caused to flow inside the plates 9 (through lines 10, 11, 13, 15) by means of pump 14.

This fluid, as a result of the thermal evolution, tends to vary in volume. These variations are made possibly by the use of an expansion chamber 16 whose level variation depends on the instantaneous volume of liquid heat carrier contained in the loop formed by elements 9, 10 and 14.

The gaseous atmosphere of 16 may consist preferably of synthesis gases which have been supplied thereto through the connecting pipe 17. The connection point of pipe 17 is chosen as close as possible to the inlet of reactor 8. This arrangement is thus one of those which provide for substantially the same pressure in the reaction zone and inside the plates wherethrough flows the liquid heat carrier.

As a matter of fact and as a result of this arrangement, the plates 9 are subjected to a differential pressure, which is either nil or at least negligible (0.1 to 0.5 MPa) as compared to the pressure prevailing in reactor 8, this pressure being, for example, from about 5 to 10 MPa for the methanol synthesis, or from about 20 to 100 MPa for the ammonia synthesis.

In view of this low differential pressure, the plates 9 may merely consist of two plane sheet iron plates whose spacing may be achieved, for example, by means of a web or internal structure either of corrugated sheet iron or of expanded metal, thus forming channels inside the plate, said channels giving their strength to plates which may reach or even exceed 10 meters of height, for example.

Figure 2:
FIGS. 2, 2A and 2B respectively illustrate alternative embodiments of the sheet iron webs employed in the invention.
Figure 2A:
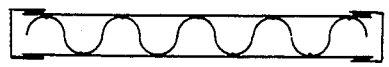
Figure 2B:

In order to impart a good turbulence to the fluid heat carrier, through the so-formed channels, the sheet iron web may have various shapes, as shown for example in FIG. 2 (channels whose cross-section is substantially of rectangular or square shape) or in FIG. 2A (channels whose cross-section has substantially a curvilinear, cylindrical, elliptical or circular shape) or in FIG. 2B (channels whose section has substantially a triangular shape).

The assembling of the sheet iron elements may be effected either by welding or, much more economically, by brazing by points or by immersion into a bath, or any other convenient technique.

Figure 3:
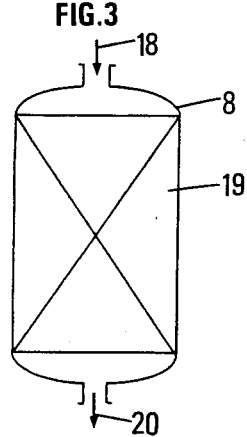
FIG. 3 shows a reactor of axial type with a catalyst bed therein.
Figure 4:
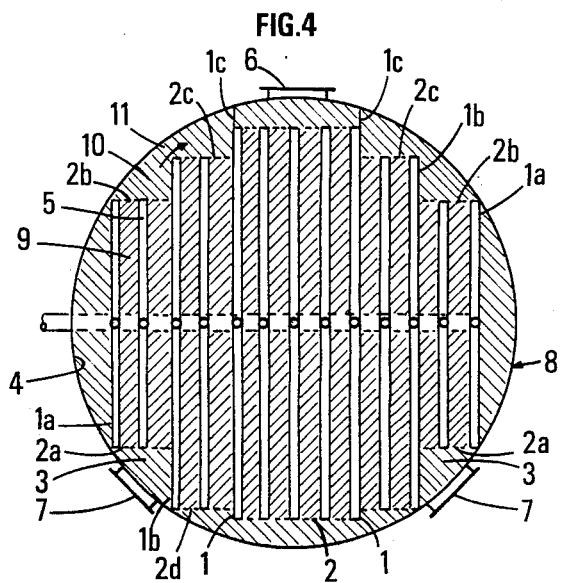
FIGS. 4 and 4A are alternative embodiments.

In FIG. 1, as in FIG. 3, pipe 18 for the gas supply has been arbitrarily placed at the top of the reactor and pipe 20 for withdrawing the reaction effluent at the bottom of the reactor; but these pipes 18 and 20 may in fact be located at any convenient level of the reactor, as will be shown for example in FIG. 4. The catalyst supply into the reactor is effected in a conventional manner, either when fixed beds or moving beds or fluid beds or boiling beds are involved.

Generally reactors of the axial type are used.

FIG. 3 diagrammatically shows a reactor 8 of the axial type with catalyst beds 19, the inlet 18 and the outlet 20 for the reactants.

The reactor of axial type is sometimes preferred for relatively low gas flow rates (a reactor of the radial type is sometimes chosen for relatively high gas flow rates).

It is obvious that the level at which the fluid heat carrier is supplied and its withdrawing level (which in the case of FIG. 1 are respectively at the upper part for the supply and at the lower part for the withdrawal) are selected at will in upper or lower position. The arrangement of the plates, according to the invention, is illustrated in FIG. 4 and in the corresponding cross-selectional view of FIG. 4A.

The catalyst is enclosed into spaces of parallelipiped shape defined by heat exchange plates 1a, 1b, 1c, etc . . . and permeable walls 2a, 2b, 2c, etc . . . . These spaces are included within a circle coaxial to the circle defined by the circular section of the reaction zone.

The walls 1a and 1b form with the lower wall 4 of the reactor a connection tight to the gases introduced, through at least one line 7, into spaces 3. Accordingly, the synthesis gases are obliged to pass through a permeable wall such as 2a before contacting the catalyst.

At the contact with the catalyst, the gases combine with each other and their temperature tends to evolve.

In order to prevent this evolution, intermediate plates 5 may be arranged in addition to the wall-forming plates 1a and 1b. The number of these plates 5 depends obviously on the heat amount involved in the reaction.

The gases flow out through permeable walls such as 2b and pass through the catalyst contained between walls 1b and 1c.

Accordingly, they pass through slots defined by walls 1b and the inner wall 4 of the reactor. This phenomenon occurs again through all the spaces of parallelipiped shape and, finally, the gases flow out through at least one opening 6 provided in the wall 4 of reactor 8.

The reactor may be described more in detail as follows (with reference to FIGS. 4 and 4A);

The cylindrical reactor (8) for chemical synthesis is subdivided into several catalyst-containing compartments 9 of parallelipiped shape.

These compartments are defined by tight walls such as 1a, 1b, 1c, etc . . . which are the above-described plates wherethrough flows the fluid heat carrier and by permeable walls 2a, 2b, 2c, etc . . . the latter being only shown in the cross-sectional view of FIG. 4. The permeable walls may consist of either of wires in parallel or cross arrangement, or of perforated or cellular plates, or of any other equivalent type.

The compartments (9) (defined by two walls 1 ad two walls 2) are filled with solid catalyst, for example a catalyst for synthesizing ammonia from hydrogen and nitrogen, or for the synthesis of methanol and/or homologous alcohols from hydrogen, carbon monoxide and optionally carbon dioxide.

The fresh gases (e.g. either a mixture of hydrogen and nitrogen or a mixture of hydrogen and carbon oxides) at a conveniently adjusted pressure and temperature, are introduced through at least one line 7 into the spaces 3 arranged between the cylindrical wall 4 of the reactor and the walls 1 and 2 of the catalytic compartments.

From the spaces 3, the gases pass through the permeable walls 2 for being in contact with the catalyst.

The sectional areas of the compartments is so selected as to obtain a sufficient velocity of the gas through the catalyst mass. It is known that said gas velocity depends on the homogeneity of the gas distribution and on the absence of hot point at the surface of the catalyst particles.

According to the processes of the invention, the gas velocities must preferably be from 1 to 200 meters per second, preferably from 5 to 100 meters per second.

The above-indicated gas velocities are based on the gas flow rate by volume, calculated under normal conditions of pressure and temperature i.e. under atmospheric pressure and at 0° C.

At the outlet of the one or more first compartments (defined by the walls 2a, 1a, 2b and 1b), the gases penetrate into the void space 10 which is similar to the void space 3 at the inlet.

From a space such as 10, the gases pass through an opening (or port), such as 11, provided between the wall 1 and the wall 4 of the reactor and from there to the one or more compartments (defined by the walls 1b, 2c, 1c, 2d) and so on.

In the embodiment of FIG. 4, the gas is symmetrically distributed with respect to the diameter of the reactor. It is obvious that a continuous circulation from one end to the other end of the reactor is also within the scope of the invention.

The reaction gases thru flow progressively through each of the enclosures 9 substantially perpendicularly to the axis of the reaction zone.

In all the figures the reactor is shown in vertical position but, in some cases, an oblique or even horizontal position of the reactor may be advantageous. This is, for example, the case when making use of a very elongate reactor wherein the static pressure is substantially different at the top and at the bottom.

In the case of radial reactors, this pressure difference results in an uneven distribution of the gas that different inventions have attempted to cope with (U.S. Pat. No. 3,754,078, British Pat. No. 1 118 750).

In view of the good control of the flow rate, in the case of this invention, this problem is less important. However, for a reactor of very large size, the horizontal arrangement may be of interest.

In FIG. 4, the cylindrical wall 4 of the reactor is simple and one-piece made. But, for example, in the case of ammonia synthesis, in order to avoid a decrease of the wall strength as a result of a too high temperature, the reactor wall may be lined or its strength increased by any convenient device.

When the catalyst is used under severe conditions of pressure and temperature, the problems of loading and discharging the catalyst are very important. Thus, in the reactor of FIG. 4A, the chambers 9 of parallelipiped shape may be closed at both of their ends so that the gases cannot pass from one chamber to another through said ends. This can be achieved by the provision of a tight plate such a 12 at each of the axial ends of said chambers (only one of these plates is shown).

One of the advantages of the process of the invention is to provide for the loading and discharge of the catalyst without disassembling the reactor and its internal parts.

Figure 4A:
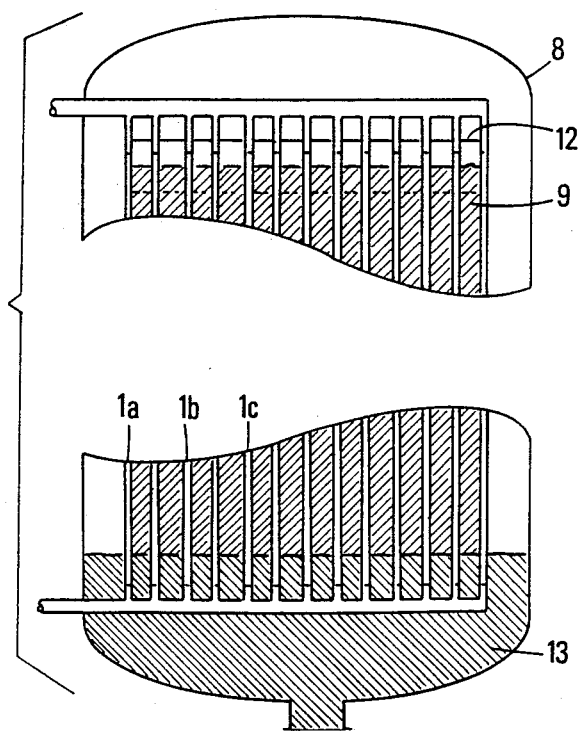

The catalyst withdrawal is particularly easy according to the embodiment shown in FIG. 4A.

In this embodiment, the bottom of the compartments of parallelipiped shape, instead of consisting of a flat bottom, is generally formed of a layer 13 of solid particles filling the generally elliptic bottom of the reactor: these particles are characterized in that their average diameter in said layer is from one half to one thousandth of the average diameter of the catalyst particles forming the catalyst bed and preferably from one fifth to one hundreth of said average diameter.

These solid particles may consist at least partially either of catalyst reduced to powder, or of metals, or of inert materials, such as alumina or carborundum or any equivalent solid.

In the present process, the gas charge may be introduced either the top or at the bottom or at any point of the reactor wall, provided that said charge is subsequently distributed vertically along the permeable inlets of the catalyst enclosures.

The reactors may contain several superposed catalyst beds, each bed being accompanied with the device according to the invention.

The details of the invention as stated in the appended claims must be considered as forming part of the present description.

What is claimed as the invention is:

1. A process for effecting chemical syntheses from reaction gases in gaseous phase and under pressure in a reaction zone (8, see FIGS. 4 and 4A) defined by an enclosure of substantially cylindrical shape and of substantially circular transverse cross-section, the process being carried out in the presence of a solid catalyst, and said process being characterized in that the reaction zone is divided into a plurality of enclosures (9) containing the catalyst therein, said enclosures being shaped as elongate parallelipipeds and located adjacent to each other, the transverse cross-sections of these enclosures being substantially included in a circle coaxial to the circle defined by the circular section of the reaction zone, the adjacent walls (1, such as 1a, 1b, 1c) of these enclosures or walls common to adjacent enclosures being tight to the gases flowing through the reaction zone, the side walls (2, such as 2a, 2b, 2c, etc . . . ) of said enclosures (9) being permeable to the gases, with the gases introduced in the reaction zone thus flowing progressively through each of the enclosures substantially perpendicularly to the axis of the reaction zone, and these gases penetrating into each enclosure (9) through a permeable wall and issuing therefrom through a permeable wall opposite to the wall wherethrough the gases are admitted, the process being further characterized in that said walls (1, such as 1a, 1b, 1c, etc . . . ) are hollow plates whose internal spaces communicate with each other, and comprising flowing a fluid heat carrier through said walls or plates under a pressure substantially equal to the pressure to which are subjected the reaction gases.

2. A process according to claim 1, wherein the fluid heat carrier flows in each of said hollow plates through a network of substantially parallel channels whose sections have a shape selected from at least one of the following shapes: square, rectangular, curvilinear, cylindrical, elliptical, circular or triangular.

3. A process according to claim 1, wherein fresh gases or a gas charge penetrate into the reaction zone (8) through two lines (7) at the vicinity of each of the two first enclosures (9) the most remote from each other, hence the most remote from the axis of the reaction zone, said two first enclosures being diametrically opposite to each other, the gases or the charge then penetrating into each of these two enclosures, through the two permeable walls (2a) of each of said enclosures, the gases or the charge flowing thereafter inside the two first enclosures (9) in the direction of the second permeable wall (2b) of each of said two fist enclosures, the gases leaving each of these two first enclosures through said so-called permeable second wall (2b) and penetrating into another enclosure (9), adjacent to the two first enclosures, through one of the two permeable walls (2c) of said other enclosure, said permable walls being those in the immediate vicinity of said permeable walls (2b) wherethrough said gases were issuing from said first enclosures, the gases thus flowing, in two separate streams, progressively through the other enclosures (9), penetrating into each enclosure (9) through one of its permeable walls and issuing through the other permeable wall, thus reaching the one or more elongate central enclosures (9), which are arranged substantially along one of the diameter of the circular section of the reaction zone, wherefrom they are subsequently withdrawn through a line (6) as reaction effluent.

4. A process according to claim 1, wherein the velocity of the gases inside said enclosures is from about 1 to 200 meters/second.

5. A process according to claim 1, wherein the reaction zone is arranged substantially vertically.

6. A process according to claim 1, wherein the reaction zone is arranged substantially horizontally.

7. A process according to claim 1, wherein the lower part of the reaction zone, into which said inclosures penetrate at least partially, is filled with a layer of solid particles havin an average diameter from one half to one thousandth the average diameter of the catalyst particles.

8. A process according to claim 1, wherein, in order to maintain substantially equal the pressure of the reaction gases and the pressure at which is subjected the fluid heat carrier, the internal spaces of the hollow plates wherethough flows said fluid heat carrier are in contact with an expansion chamber whose level varies in accordance with the instantaneous volume of liquid heat carrier in said plates, the gaseous atmosphere of the expansion chamber consisting of reaction gases reaching said chamber through an adequate by-pass in communication with the reaction space in the reaction zone.

9. A process according to claim 1, wherein nitrogen and hydrogen are passed through the catalyst-containing enclosures, thereby forming ammonia.

10. A process according to claim 1, wherein hydrogen and at least one carbon oxide are passed through the catalyst-containing zones, thereby synthesizing methanol or higher homologue alcohols thereof.

11. A process for effecting chemical synthesis reactions from reaction gases in gaseous phase and under pressure in a reaction zone (8, see FIGS. 4 and 4A) defined as an enclosure of substantially cylindrical shape and of substantially circular transverse cross-section, the process being carried out in the presence of a solid catalyst, said process comprising circulating said reaction gases into the reaction zone (8) divided into a plurality of enclosures (9) containing the catalyst, said enclosures, being defined by adjacent walls (1, axial side walls such as 1a, 1b, 1c . . . ) parallel to one another and by side walls (2, axial end walls such as 2a, 2b, 2c . . . ) parallel to one another, said enclosures (9) being shaped as elongate parallelipipeds, substantially parallel to the axis of the reactor cylinder, and being adjacent to each other, the transverse cross-sections of the enclosures being substantially included in a circle coaxial to the circle defined by the circular section of the reaction zone, the adjacent walls (1) of these enclosures, or the common walls of the adjacent enclosures, being tight to the gases flowing through the reaction zone and forming a deflected path wherethrough the gas is compelled to flow, said side walls (2, axial end walls such as 2a, 2b, 3c . . . ) of said enclosures (9) being permeable to the gases, with these gases penetrating into each enclosure (9) through a permeable wall and issuing therefrom through a permeable wall opposite to the wall wherethrough the gases are admitted, flowing as a result progressively through each of the enclosures substantially perpendicular to the axis of the reaction zone, and said process comprising circulating a fluid heat carrier through said walls (1) which are hollow plates whose internal spaces communicate with each other, under a pressure substantially equal to the pressure to which are subjected the reaction gases.

12. A process according to claim 11, wherein the fluid heat carrier flows in each of said hollow plates through a network of substantially parallel channels whose sections have a shape selected from at least one of the following shapes: square, rectangular, curvilinear, cylindrical, elliptical, circular or triangular.

13. A process according to claim 11, wherein nitrogen and hydrogen are passed through the catalyst-containing enclosures, thereby forming ammonia.

14. A process according to claim 11, wherein hydrogen and at least one carbon oxide are passed through the catalyst-containing zones, thereby synthesizing methanol or higher homologue alcohols thereof.

15. A process according to claim 11, wherein the reaction zone is arranged substantially vertically.

16. A process according to claim 11, wherein the reaction zone is arranged substantially horizontally.

* * * * *